US012758197B2

(12) United States Patent
Park et al.

(10) Patent No.: US 12,758,197 B2
(45) Date of Patent: Oct. 13, 2026

(54) MICROSTRUCTURE FOR ACTIVELY SAMPLING MICROBE AND METHOD FOR ACTIVELY SAMPLING MICROBE BY USING SAME

(71) Applicant: DAEGU GYEONGBUK INSTITUTE OF SCIENCE AND TECHNOLOGY, Daegu (KR)

(72) Inventors: Suk Ho Park, Gwangju (KR); Su Hyun Kwon, Daegu (KR); Deock Hee Yoon, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 473 days.

(21) Appl. No.: 18/287,335

(22) PCT Filed: Mar. 18, 2022

(86) PCT No.: PCT/KR2022/003796
§ 371 (c)(1),
(2) Date: Dec. 13, 2023

(87) PCT Pub. No.: WO2022/225193
PCT Pub. Date: Oct. 27, 2022

(65) Prior Publication Data
US 2024/0188940 A1 Jun. 13, 2024

(30) Foreign Application Priority Data
Apr. 23, 2021 (KR) ........................ 10-2021-0052988

(51) Int. Cl.
*A61B 10/00* (2006.01)

(52) U.S. Cl.
CPC .. *A61B 10/0045* (2013.01); *A61B 2010/0061* (2013.01)

(58) Field of Classification Search
CPC ........ A61B 10/0045; A61B 2010/0061; A61B 5/00; A61B 10/00; A61B 5/4255; A61B 5/6861; A61B 2562/162; C12Q 1/24; C12Q 1/689; B03C 2201/22
See application file for complete search history.

(56) References Cited

U.S. PATENT DOCUMENTS

2023/0181172 A1* 6/2023 Srivastava ......... A61B 10/0096 424/400

FOREIGN PATENT DOCUMENTS

| | | | |
|---|---|---|---|
| CN | 109536571 | 3/2019 | |
| CN | 111423051 | 7/2020 | |
| EP | 2508171 A1 * | 10/2012 | ........... A61K 31/122 |

(Continued)

OTHER PUBLICATIONS

Waimin et al. ("Smart capsule for non-invasive sampling and studying of the gastrointestinal microbiome") (Year: 2020).*

*Primary Examiner* — Christian Jang
(74) *Attorney, Agent, or Firm* — LEX IP MEISTER, PLLC

(57) ABSTRACT

Various embodiments of the present invention pertain to a microstructure for actively sampling microbes, which can easily sample and recover intestinal microbes, and a method of actively sampling microbes by using same. The microstructure for actively sampling microbes may comprise: a core including magnetic nanoparticles, a reaction initiator, and a polymer monomer; and a shell surrounding the core and including a fatty acid.

15 Claims, 5 Drawing Sheets

(56) References Cited

FOREIGN PATENT DOCUMENTS

| | | |
|---|---|---|
| JP | 2003210158 | 7/2003 |
| KR | 10-2011-0058711 | 6/2011 |
| WO | 2019240045 | 12/2019 |

* cited by examiner

MICROSTRUCTURE FOR ACTIVELY SAMPLING MICROBE AND METHOD FOR ACTIVELY SAMPLING MICROBE BY USING SAME

TECHNICAL FIELD

Embodiments relate to a microstructure for actively sampling microbes and a method of actively sampling microbes using the same. More specifically, embodiments relate to a microstructure for actively sampling microbes that can easily sample and recover intestinal microbes and a method of actively sampling microbes using the same.

BACKGROUND ART

It is reported that there are more than 500 species and more than 10 trillion intestinal bacteria in the human intestine and that the weight of intestinal bacteria is up to 2 kg. Based on results of research showing that microbes living in the human body have a very great influence on the human body, research is actively underway on intestinal microbes to analyze the genetic information of microbes. It is known that various microbes in the human body affect all functions of the human body, including regulation of biological metabolism, digestive ability, and various diseases, as well as genetic modification due to environmental changes and the passage of genes to the next generation. In particular, various metabolic and immune diseases related to allergies, rhinitis, atopy, and obesity, enteritis and heart disease are reported to be related to these intestinal microbes.

One method of sampling intestinal microbes is to take capsules for sampling microbes. In other words, the capsules for sampling microbes sample intestinal fluid from the intestines, discharge the fluid to the body through peristalsis of the digestive system, and collect the fluid. However, these capsules have structural defects and limitations because the capsules must be manufactured in a size that can be taken by patients in order to achieve this. Recently, capsules having a size of 2 cm or less have been developed, but the size thereof is still burdensome to swallow and problems with insufficient stability and reliability for use in the human body.

In addition, since the distribution of microbes changes depending on the location in the intestines, the capsules must be moved to the desired location in order to sample microbes from the specific location in the intestines. However, conventional capsules have the disadvantage of difficulty in location regulation. In addition, research on methods of collect the microbes which are sampled by capsules and then discharged to the outside of the body remains insufficient.

DISCLOSURE

Technical Problem

It is an object of the present invention to provide a microstructure for actively sampling microbes that can easily sample and recover intestinal microbes and a method of actively sampling microbes using the same.

Technical Solution

In accordance with one aspect of the present invention, the above and other objects can be accomplished by the provision of a microstructure for actively sampling microbes including a core containing magnetic nanoparticles, a reaction initiator, and a polymer monomer, and a shell surrounding the core and containing fatty acid.

In some embodiments of the present invention, the magnetic nanoparticles may contain at least one metal element selected from the group consisting of Fe, Ni, Pt, Au, Cr, Co, Gd, Dy, and Mn.

In some embodiments of the present invention, the reaction initiator may contain ascorbic acid and ferric chloride.

In some embodiments of the present invention, the polymer monomer may include at least one selected from the group consisting of poly(ethylene glycol) diacrylate (PEGDA), hexane-1,6-diol diacrylate (HDDA), ethoxylated trimethylolpropane triacrylate (ETTA), and ethylene carbonate (EC).

In some embodiments of the present invention, the fatty acid may have a melting point of 40° C. to 50° C.

In some embodiments of the present invention, the fatty acid may include at least one selected from the group consisting of caprylic acid, capric acid, lauric acid, myristic acid, palmitic acid, stearic acid, arachidic acid, behenic acid, and lignoceric acid.

In some embodiments of the present invention, the magnetic nanoparticles, the reaction initiator, and the polymer monomer may be present at a weight ratio of 0.05 to 0.15:0.90 to 1.00:0.75 to 0.85.

In some embodiments of the present invention, the microstructure may have a diameter of 0.2 mm to 2 mm.

In some embodiments of the present invention, the shell may have a thickness of 10 nm to 100 nm.

In accordance with another aspect of the present invention, provided is a method of actively sampling microbes using the microstructure according to some embodiments of the present invention including: preparing a microstructure including a core containing magnetic nanoparticles, a reaction initiator, and a polymer monomer, and a shell surrounding the core and containing fatty acid; administering the microstructure to a subject; applying an external magnetic field to the microstructure to move the microstructure to a location for sampling microbes; applying an external stimulus thereto; melting fatty acid of the microstructure; adsorbing microbes to the microstructure; discharging the microstructure containing the microbes adsorbed thereto to an outside of the subject; and recovering the microstructure containing the microbes adsorbed thereto through an external magnetic field.

In some embodiments of the present invention, in the applying the external stimulus thereto, the magnetic nanoparticles may be heated.

In some embodiments of the present invention, the external stimulus may be an alternating magnetic field (AMF) or near infrared (NIR).

In some embodiments of the present invention, the melting the fatty acid may include exposing the core of the microstructure to absorb water into the organ and thereby cause a radical polymerization reaction.

In some embodiments of the present invention, in the adsorbing microbes to the microstructure, the microbes may be adsorbed by hydrogel formed by the radical polymerization reaction.

In some embodiments of the present invention, the microstructure containing the microbes adsorbed thereto may contain the hydrogel, the adsorbed microbes and the magnetic nanoparticles.

Advantageous Effects

The microstructure according to some embodiments of the present invention has a very small size and can be easily taken directly. In addition, the microstructure is imparted with magnetism and can be moved to a desired location inside the organ. Therefore, microbes can be sampled from various locations inside the organ using the microstructure of the present invention and can thus be used for research or diagnosis.

When the microstructure according to some embodiments of the present invention is heated by an external stimulus, the shell containing fatty acid may be melted, resulting in self-assembly and hydrogelation through a radical polymerization reaction and easy collection of intestinal microbes. In addition, the microstructure to which microbes are adsorbed can be easily recovered using an external magnetic field upon microbial recovery after being discharged from the body. The recovered microstructure to which the microbes is adsorbed can be used for research, diagnosis and treatment on the distribution of intestinal microbes through genetic analysis.

BEST MODE

Hereinafter, reference will be made in detail to various embodiments of the present invention, examples of which are illustrated in the accompanying drawings and described below. In addition, it should be understood that embodiments and the terms used therein do not limit technical features disclosed herein to specific aspects and include various alternatives, modifications, and/or equivalents thereof.

Hereinafter, embodiments of the present invention will be described in detail with reference to the attached drawings.

Figure 1:
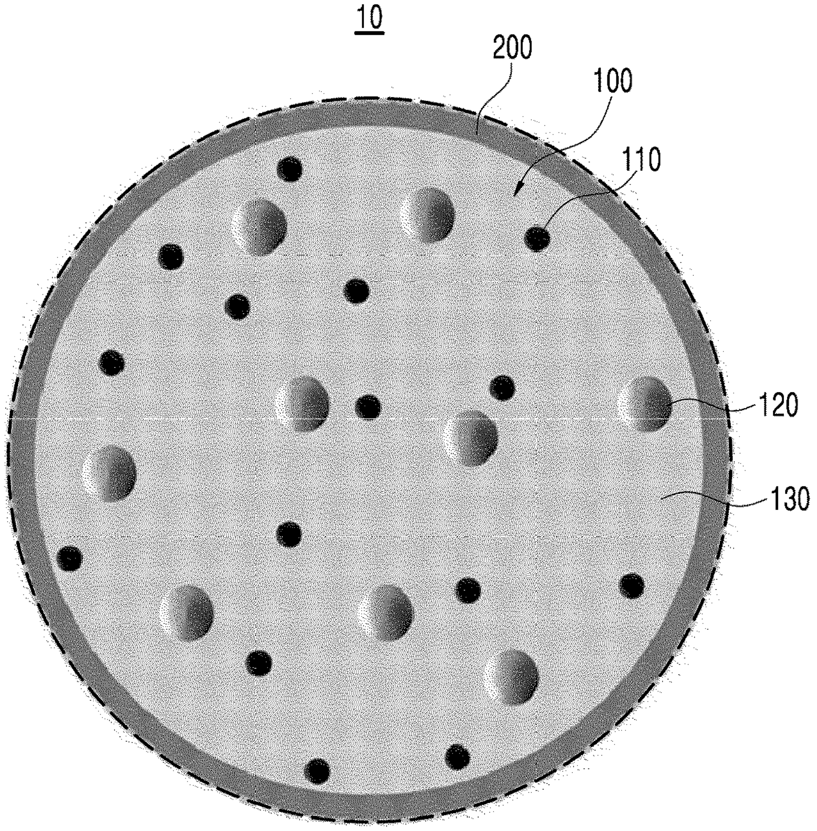
FIGS. 1 and 2 illustrate a microstructure according to various embodiments of the present invention.

Referring to FIG. 1, the microstructure 10 for actively sampling microbes according to some embodiments of the present invention includes a core 100 and a shell 200. The microstructure 10 may be spherical.

The core 100 may contain magnetic nanoparticles 110, a reaction initiator 120, and a polymer monomer 130.

In this case, the magnetic nanoparticles 110 may contain at least one metal element selected from the group consisting of Fe, Ni, Pt, Au, Cr, Co, Gd, Dy, and Mn. Specifically, the magnetic nanoparticles 110 may contain at least one of $Fe_2O_3$ and $Fe_3O_4$. The position of the magnetic nanoparticles 110 may be changed by an external magnetic field and may be heated by an external stimulus such as an alternating magnetic field (AMF) or near infrared (NIR).

The reaction initiator 120 may contain ascorbic acid and ferric chloride. The reaction initiator 120 may contact moisture in intestinal fluid to induce a radical polymerization reaction and self-assembly.

The polymer monomer 130 may include at least one selected from the group consisting of poly(ethylene glycol) diacrylate (PEGDA), hexane-1,6-diol diacrylate (HDDA), and ethoxylated trimethyl ethoxylated trimethylolpropane triacrylate (ETTA), and ethylene carbonate (EC). The polymer monomer 130 can synthesize a hydrogel through the radical polymerization reaction induced by the reaction initiator 120.

The reaction initiator 120 and the polymer monomer 130 in the core 100 may be present in a molar ratio of 1:0.5 to 1.5. The magnetic nanoparticles 110, the reaction initiator 120, and the polymer monomer 130 in the core 100 may be present in a weight ratio of 0.05 to 0.15:0.90 to 1.00:0.75 to 0.85. Preferably, the magnetic nanoparticles 110, the reaction initiator 120, and the polymer monomer 130 in the core 100 may be present in a weight ratio of 0.10:0.95:0.82. When the magnetic nanoparticles 110 are present in the weight ratio defined above, sufficient magnetism can be imparted to the microstructure 10 and position movement can be facilitated by the external magnetic field. In addition, when the polymer monomer 130 is present at the weight ratio defined above, hydrogelation can easily occur and intestinal microbes can be easily sampled upon exposure of the core 100 after the microstructure 10 is disposed in the intestine.

The shell 200 may surround the core 100. The shell 200 may coat the surface of core 100. The shell 200 may physically and stably coat the core 100 through hydrogen bonding and weak interaction. The shell 200 may contain saturated fatty acid. The shell 200 may contain fatty acid having a melting point of 40° C. to 50° C. That is, the shell 200 may contain saturated fatty acid which is not melted in the human body but melted when heat is generated. Accordingly, the shell 200 can protect the microstructure 10 from bodily fluids until it moves to the target location in the intestine. For example, the fatty acid includes at least one selected from the group consisting of caprylic acid (mp=16.7° C.), capric acid (mp=31.6° C.), lauric acid (mp=44.2° C.), myristic acid (mp=53.9° C.), palmitic acid (mp=63.1° C.), stearic acid (mp=69.6° C.), arachidic acid (mp=76.5° C.), behenic acid (mp=80.0° C.), and lignoceric acid (mp=86.0° C.). Preferably, the fatty acid may be lauric acid.

In this case, the thickness of the shell 200 containing fatty acid may be 10 nm to 100 nm. Based on the thickness of the shell 200 containing fatty acid, the core can be safely protected up to the target location in the intestines, the saturated fatty acid can be sufficiently melted by heat generation from the magnetic nanoparticles through external stimulation, and the material of the core 100 can be exposed to intestinal fluid.

The microstructure 10 may be produced by mixing the magnetic nanoparticles 110, the reaction initiator 120, and the polymer monomer 130, homogeneously dispersing these components, and then dropping the resulting dispersion into a liquid phase in which fatty acid is melted to coat the dispersion with the fatty acid. Specifically, first, the polymer monomer 130 may be prepared by vacuum drying at 50° C. for 12 hours. The reaction initiator 120 may be prepared by vacuum drying at 50° C. for 12 hours. Then, the polymer monomer 130, the reaction initiator 120, and the magnetic nanoparticles 110 may be mixed and vacuum-dried at 50° C. for 12 hours to prepare a mixture. 10 g of the prepared mixture is mixed with and dissolved in 0.5 m to 1 ml of anhydrous DMF, the resulting solution is dropped in anhydrous ether, and the resulting mixture is vacuum-dried to prepare a material of the core 100. The material of the core 100 is added to a solution of fatty acid in a solvent (e.g., toluene, 1-octadecane, or benzyl ether), stirred well at 100° C. for one hour, filtered, and then vacuum dried to produce a microstructure 10.

The microstructure 10 of the present invention has a very small size and can be easily taken directly. For example, the microstructure 10 of the present invention may have a size of 0.2 mm to 2 mm. In addition, the microstructure 10 is imparted with magnetism and can be moved to a desired location inside the organ. Therefore, microbes can be sampled from various locations inside the organ using the microstructure 10 of the present invention and can thus be used for research or diagnosis.

Figure 2:
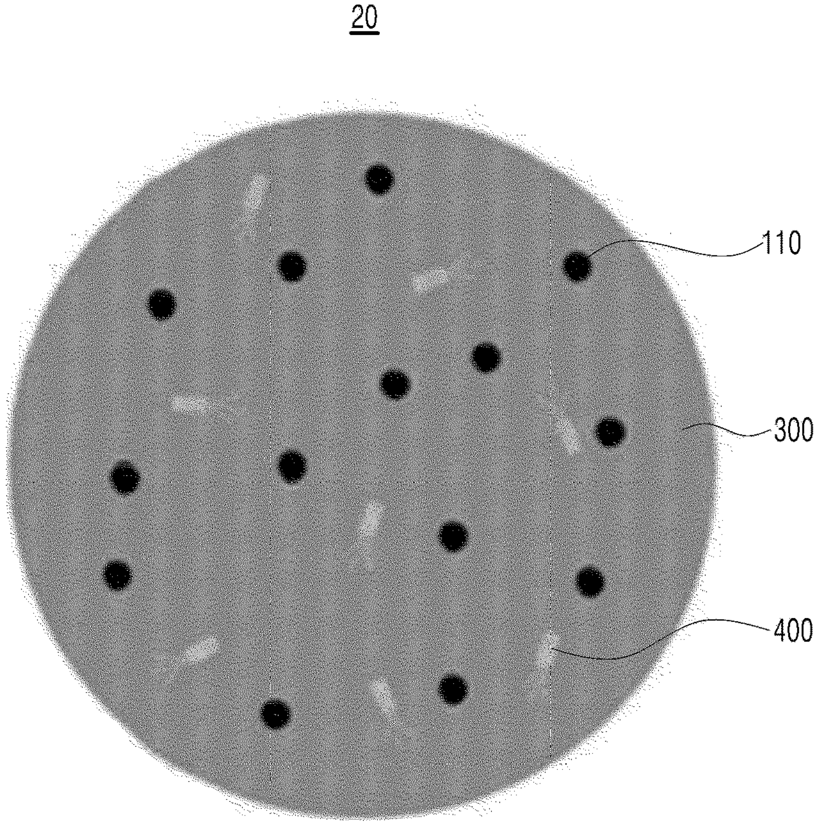

When the microstructure 10 of the present invention comes into contact with intestinal fluid and then absorbs the intestinal fluid, the initiator 120 induces self-assembly through a radical polymerization reaction and the polymer monomer 130 is hydrogelated to capture microbes contained in the intestinal fluid. The microstructure 20 to which microbes 400 are adsorbed is shown in FIG. 2. Referring to FIG. 2, the microstructure 20 to which the microbes 400 are adsorbed may be a particle containing the magnetic nanoparticles 110 and the hydrogel 300 containing the microbes 400. Since the microstructure 20 to which the microbes 400 is adsorbed contains magnetic nanoparticles 110, microbes can be easily recovered using an external magnetic field after the microstructure is discharged from the body.

Hereinafter, a method of actively sampling microbes using the microstructure according to some embodiments of the present invention will be described in detail with reference to FIGS. 3 to 7.

Figure 3:
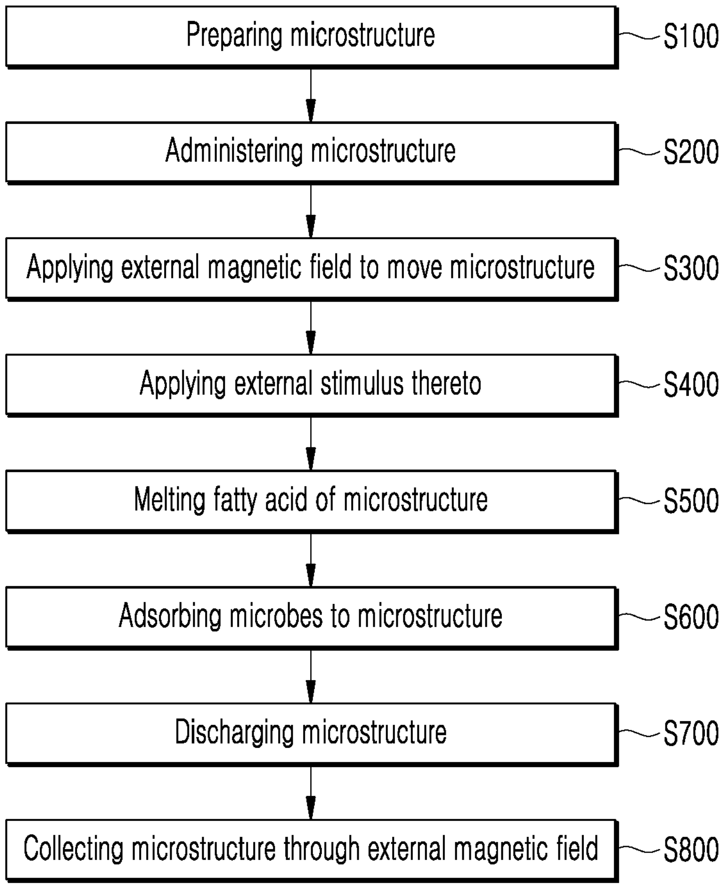
FIG. 3 is a flowchart illustrating a method of actively sampling microbes according to some embodiments of the present invention.

Referring to FIG. 3, the method of actively sampling microbes includes producing a microstructure (S100), administering the microstructure to a subject (S200), applying an external magnetic field to the microstructure to move the microstructure (S300), applying an external stimulus to the microstructure (S400), melting fatty acid of the microstructure (S500), adsorbing microbes to the microstructure (S600), discharging the microstructure containing the microbes adsorbed thereto to an outside of the subject (S700), and recovering the microstructure containing the microbes adsorbed thereto through an external magnetic field (S800).

First, in the step of preparing a microstructure (S100), the microstructure 10 may be prepared as described above. That is, the microstructure 10 including a core 10 containing magnetic nanoparticles 110, a reaction initiator 120, and a polymer monomer 130, and a shell 20 containing fatty acid may be prepared.

In the step of administering the microstructure to the subject (S200), a large number (tens to hundreds) of microstructures may be directly administered to a subject in need of microbial sampling through the esophagus or the like.

Figure 4:
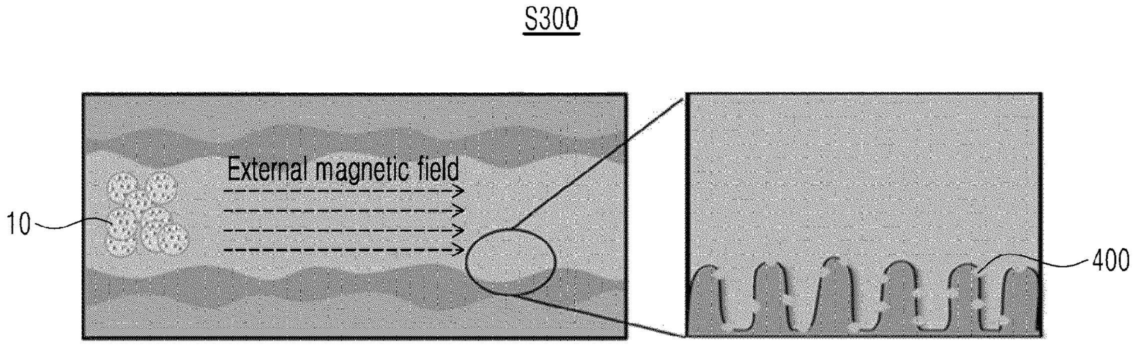
FIGS. 4 to 7 illustrate a method of actively sampling microbes according to some embodiments of the present invention.

Referring to FIG. 4, in the step of applying an external magnetic field to the microstructure 10 to move the microstructure (S300), the microstructure 10 may be moved to a target location within an organ in need of microbial sampling through the external magnetic field and the microstructure 10 may be accumulated.

Figure 5:
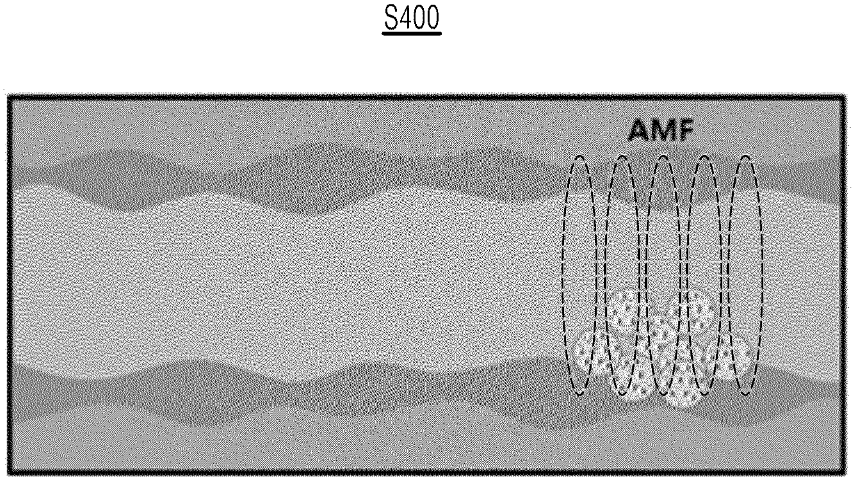

Referring to FIG. 5, in the step of applying an external stimulus to the microstructure 10 (S400), the external magnetic field may be removed and then an external stimulus such as an alternating magnetic field (AMF) or near infrared (NIR) may be applied to the microstructure 10. Heat may be generated by the magnetic nanoparticles of the microstructure 10 through such external stimulation.

In the step of melting the fatty acid of the microstructure (S500), the shell 200 containing the fatty acid of the microstructure may be melted by heat generation of the magnetic nanoparticles due to external stimulation. As a result, the core 100 may be exposed to intestinal fluid.

Figure 6:
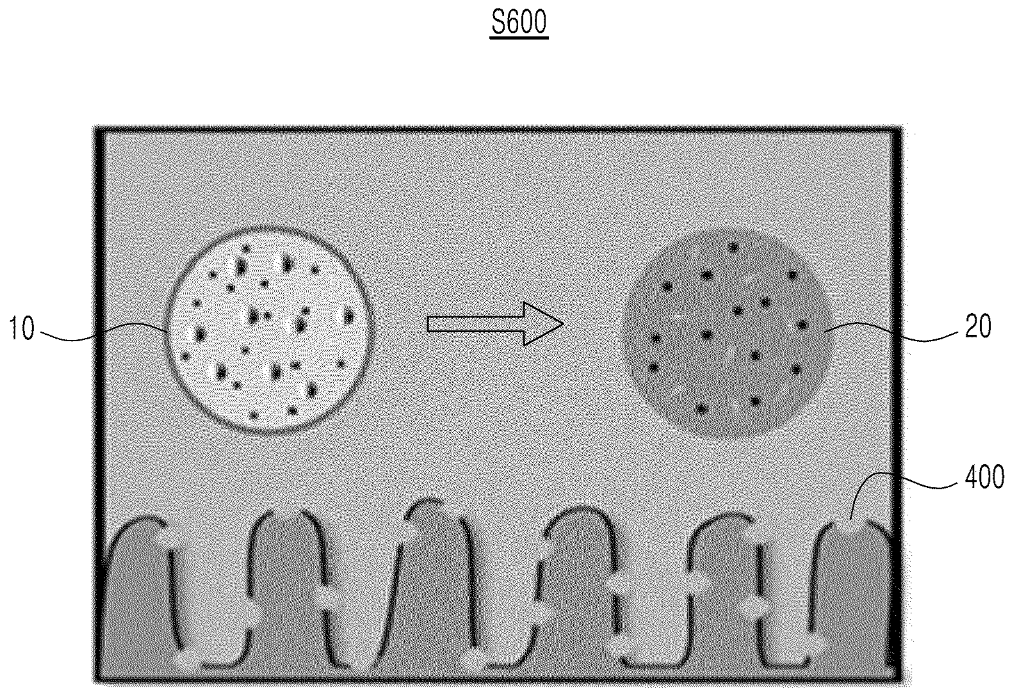

Referring to FIG. 6, in the step of adsorbing microbes (S600), self-assembly may be induced through a radical polymerization reaction by the initiator of the core in the microstructure 10, and the polymer monomer may be hydrogelated to collect microbes contained in the intestinal fluid (400). That is, ultimately, the microstructure 20 may be converted into a structure containing the hydrogel, the adsorbed microbes 400, and the magnetic nanoparticles.

In the step of discharging the microstructure 20 containing microbes adsorbed thereto, the microstructure 20 containing microbes adsorbed thereto may be discharged as feces from the digestive tract through peristaltic movement of the organs.

Figure 7:
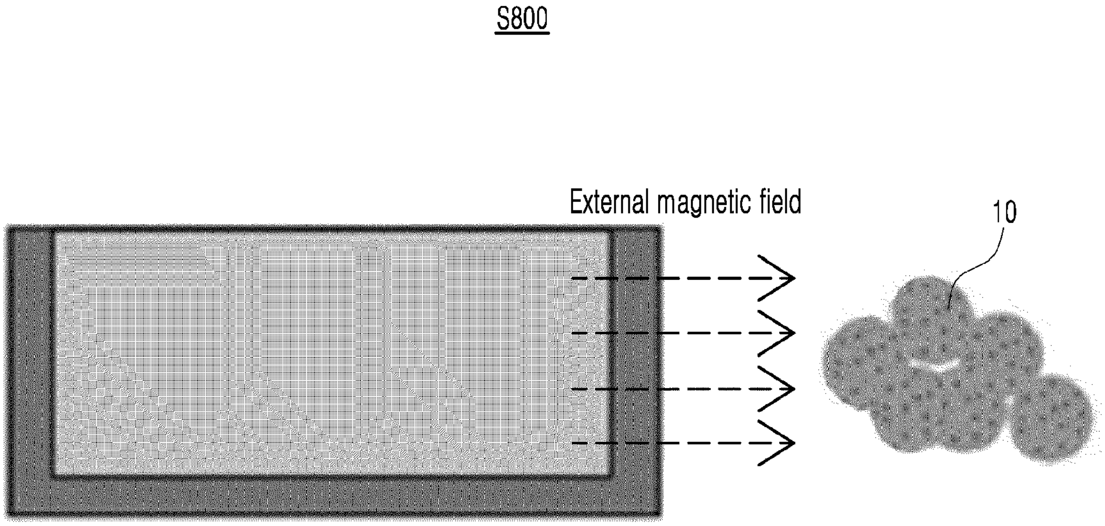

Then, referring to FIG. 7, in the step of recovering the microstructure 20 containing the microbes adsorbed thereto through an external magnetic field (S800), the discharged feces are collected and diluted, and then the microstructure 20 containing intestinal microbes adsorbed thereto can be recovered using an external magnetic field. The recovered microstructure containing the microbes adsorbed thereto is useful for research, diagnosis, and therapy based on the distribution of intestinal microbes through genetic analysis.

The features, structures, effects and the like described in the embodiments above are included in one or more embodiments of the present invention and are not necessarily limited to only one embodiment. Furthermore, the features, structures, effects, and the like illustrated in each embodiment may be combined or modified in other embodiments by those having ordinary knowledge in the field to which the embodiments pertain. Therefore, such combinations and modifications should be construed as falling within the scope of the present invention.

Although the present invention has been be described in more detail with reference to specific embodiments, the embodiments are provided only for illustration and thus should not be construed as limiting the scope of the present invention. Those skilled in the art will appreciate that various modifications, additions and substitutions are possible, without departing from the scope and spirit of the invention as disclosed in the accompanying claims. For example, each component specifically disclosed in the embodiments may be modified. In addition, these differences relating to modifications and applications should be construed as falling within the scope of the present invention as defined in the appended claims.

INDUSTRIAL APPLICABILITY

The present invention has high industrial applicability because the microstructure and the method according to the present invention are capable of accurately sampling microbes from desired target locations in organs and easily recovering the sampled microbes.

The invention claimed is:

1. A microstructure for actively sampling microbes comprising:

a core comprising magnetic nanoparticles, a reaction initiator, and a polymer monomer; and a shell surrounding the core and comprising fatty acid.

2. The microstructure according to claim 1, wherein the magnetic nanoparticles comprise at least one metal element selected from the group consisting of Fe, Ni, Pt, Au, Cr, Co, Gd, Dy, and Mn.

3. The microstructure according to claim 1, wherein the reaction initiator comprises ascorbic acid and ferric chloride.

4. The microstructure according to claim 1, wherein the polymer monomer comprises at least one selected from the group consisting of poly(ethylene glycol) diacrylate (PEGDA), hexane-1,6-diol diacrylate (HDDA), ethoxylated trimethylolpropane triacrylate (ETTA), and ethylene carbonate (EC).

5. The microstructure according to claim 1, wherein the fatty acid has a melting point of 40° C. to 50° C.

6. The microstructure according to claim 1, wherein the fatty acid comprises at least one selected from the group consisting of caprylic acid, capric acid, lauric acid, myristic acid, palmitic acid, stearic acid, arachidic acid, behenic acid, and lignoceric acid.

7. The microstructure according to claim 1, wherein the magnetic nanoparticles, the reaction initiator, and the polymer monomer are present at a weight ratio of 0.05 to 0.15:0.90 to 1.00:0.75 to 0.85.

8. The microstructure according to claim 1, wherein the microstructure has a diameter of 0.2 mm to 2 mm.

9. The microstructure according to claim 1, wherein the shell has a thickness of 10 nm to 100 nm.

10. A method of actively sampling microbes using the microstructure according to claim 1, comprising:

preparing a microstructure including a core containing magnetic nanoparticles, a reaction initiator, and a polymer monomer, and a shell surrounding the core and containing fatty acid;

administering the microstructure to a subject;

applying an external magnetic field to the microstructure to move the microstructure to a location for sampling microbes;

applying an external stimulus thereto;

melting the fatty acid of the microstructure;

adsorbing microbes to the microstructure;

discharging the microstructure containing the microbes adsorbed thereto to an outside of the subject; and recovering the microstructure containing the microbes adsorbed thereto through an external magnetic field.

11. The method according to claim 10, wherein, in the applying the external stimulus to the microstructure, the magnetic nanoparticles are heated.

12. The method according to claim 10, wherein the external stimulus is an alternating magnetic field (AMF).

13. The method according to claim 10, wherein the melting the fatty acid comprises exposing the core of the microstructure to absorb water into an organ and thereby cause a radical polymerization reaction.

14. The method according to claim 13, wherein, in the adsorbing microbes to the microstructure, the microbes are adsorbed by a hydrogel formed by the radical polymerization reaction.

15. The method according to claim 10, wherein the microstructure containing the microbes adsorbed thereto contains the hydrogel, the adsorbed microbes, and the magnetic nanoparticles.

* * * * *